US006258346B1

(12) United States Patent
Scavone et al.

(10) Patent No.: US 6,258,346 B1
(45) Date of Patent: *Jul. 10, 2001

(54) COSMETIC STICKS CONTAINING TRIGLYCERIDE GELLANTS HAVING IMPROVED PRODUCT HARDNESS AND LOW RESIDUE PERFORMANCE

(75) Inventors: Timothy Alan Scavone, Loveland; James David Landgrebe, Madeira; Eric David Dodson, West Chester, all of OH (US)

(73) Assignee: The Procter & Gamble Company, Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/573,030

(22) Filed: May 17, 2000

(51) Int. Cl.$^7$ ............... A61K 7/32; A61K 7/34; A61K 7/36; A61K 7/38; A61K 7/00
(52) U.S. Cl. ............... 424/65; 424/66; 424/67; 424/68; 424/400; 424/401
(58) Field of Search .................. 424/65, 66, 68, 424/59, 400, 401

(56) References Cited

U.S. PATENT DOCUMENTS

| | | | |
|---|---|---|---|
| 4,151,272 | 4/1979 | Geary et al. | 424/68 |
| 5,102,656 | 4/1992 | Kasat | 424/66 |
| 5,156,834 | 10/1992 | Beckmeyer et al. | 424/47 |
| 5,250,291 | 10/1993 | Park et al. | 424/66 |
| 5,449,511 | 9/1995 | Coe | 424/66 |
| 5,500,209 | 3/1996 | Ross et al. | 424/66 |
| 5,516,511 | 5/1996 | Motley et al. | 424/65 |
| 5,650,144 | 7/1997 | Hofrichter et al. | 424/66 |
| 5,718,890 | 2/1998 | Putman et al. | 424/65 |
| 5,744,130 | 4/1998 | Guskey et al. | 424/66 |
| 5,750,096 | 5/1998 | Guskey | 424/65 |
| 5,776,494 | 7/1998 | Guskey et al. | 424/484 |
| 5,833,964 | 11/1998 | Linn et al. | 424/65 |
| 5,840,286 | 11/1998 | Gardlik et al. | 424/65 |
| 5,840,288 | 11/1998 | Guskey et al. | 424/65 |
| 5,885,559 | 3/1999 | Lee et al. | 424/65 |
| 5,965,113 | 10/1999 | Guskey | 424/66 |
| 5,976,514 | 11/1999 | Guskey et al. | 424/65 |

FOREIGN PATENT DOCUMENTS

| | | |
|---|---|---|
| 1 146 867 | 5/1983 | (CA) . |
| 135315 | 4/1995 | (EP) . |
| 2299024A | 9/1996 | (GB) . |
| WO 91/04009 | 4/1991 | (WO) . |
| WO 99/16410 | 4/1999 | (WO) . |
| WO 9951192A2 | 10/1999 | (WO) . |

*Primary Examiner*—Shelly A. Dodson
(74) *Attorney, Agent, or Firm*—William J. Winter; Lucy Elandjian

(57) ABSTRACT

Disclosed are solid cosmetic stick compositions having a preferred product hardness of at least about 600 gram.force, and which comprises from about 0.01% to about 60% by weight of a cosmetic active; from about 10% to about 95% by weight of a liquid carrier; from about 1% to about 60% by weight of a solid polymorphic triglyceride gellant that within the composition is substantially free of long range crystalline order. By selecting the crystalline phase of the triglyceride gellant in the finished product, these cosmetic sticks provide improved product hardness at lower triglyceride gellant concentrations.

18 Claims, No Drawings

US 6,258,346 B1

COSMETIC STICKS CONTAINING TRIGLYCERIDE GELLANTS HAVING IMPROVED PRODUCT HARDNESS AND LOW RESIDUE PERFORMANCE

TECHNICAL FIELD

The present invention relates to cosmetic stick compositions that are formulated to contain triglyceride gellants in a crystalline phase that is substantially free of long range crystalline order. The compositions have improved hardness and low residue performance.

BACKGROUND OF THE INVENTION

There are many types of solid cosmetic sticks that are commercially available or otherwise known in the various arts. These cosmetic sticks include products such as moisturizers, perfumes or fragrances, skin conditioners, antiperspirants, anti-wrinkle products, pharmaceuticals, deodorants, make-up and foundations, sunscreens, and many other products intended for topical application to the skin. Many of these products contain a cosmetic active dispersed within a suitable liquid carrier and contained within a solid gellant or wax matrix that provides the product with sufficient hardness to form a solid stick composition. In addition to providing sufficient product hardness, the solid gellant or wax matrix also acts to contain the liquid carrier and any other liquid ingredients sufficiently to prevent syneresis of such liquids from the product form prior to application.

Wax gellants such as stearyl alcohol and other fatty alcohols are especially common in commercially available cosmetic products such as antiperspirant and deodorant sticks. These waxes typically provide a stable solid matrix within which the antiperspirant or other active and a liquid carrier can be contained with minimal or no liquid syneresis during storage. Other gellants such as triglyceride gellants have also been used in solid antiperspirant or other cosmetic sticks, due in large part to the lower raw material cost associated with the use of natural triglycerides. Many of these gellants, however, are used at relatively high concentrations to provide the stick with the desired product hardness, but such high gellant concentrations can increase raw material costs and can increased visible residue on the skin after application.

It has now been found that cosmetic sticks containing triglyceride gellants can be formulated with lower triglyceride gellant concentrations and still provide the cosmetic sticks with the desired product hardness. This is accomplished by formulating the stick composition with solid polymorphic triglycerides, wherein the polymorphic form of the gellant as formulated into the solid stick is substantially free of long range crystalline order. It has been found that by formulating these triglyceride gellants without long range crystalline order, that the product so formulated has improved product hardness at lower gellant concentrations.

It is therefore an object of the present invention to provide a solid cosmetic stick composition that contains reduced triglyceride gellant concentrations that provide the composition with improved product hardness and low residue performance. It is a further object of the present invention to formulate such a composition with a triglyceride gellant that is substantially free of long range crystalline order of the triglyceride gellant material.

SUMMARY OF THE INVENTION

The present invention is directed to solid cosmetic sticks having a preferred product hardness of at least about 600 gram.force, and which comprises from about 0.01% to about 60% by weight of a cosmetic active; from about 10% to about 95% by weight of a liquid carrier; from about 1% to about 60% by weight of a solid polymorphic triglyceride gellant that within the composition is substantially free of long range crystalline order. The present invention is also directed to solid cosmetic sticks containing fully-hydrogenated, high erucic acid, rapeseed oil (HEAR Oil)

It has been found that a triglyceride-based cosmetic sticks can be formulated at lower triglyceride concentrations provided that the triglyceride is formulated into the finished product so that it is substantially free of long range crystalline order. It has been found that these cosmetic sticks have improved product hardness at lower triglyceride gellant concentrations and provide improved low residue performance. These cosmetic sticks can also be formulated to maintain product hardness and result in little or no noticeable solvent syneresis over extended periods of time.

DETAILED DESCRIPTION OF THE INVENTION

The cosmetic stick compositions of the present invention comprise as essential ingredients a cosmetic active, a liquid carrier, and a defined crystalline form of a polymorphic triglyceride gellant. Each is described in detail hereinafter.

The term "cosmetic stick" as used herein refers generally to any stick composition suitable for topical application to the skin.

The term "anhydrous" as used herein refers to those materials or compositions that contain less than about 5%, more preferably less than about 3%, even more preferably less than about 1%, most preferably zero percent, by weight of free or added water, e.g. water other than the water of hydration typically associated with some solid materials such as particulate antiperspirant active.

The term "solid" as used herein, unless otherwise specified, refers to those materials that are solid at or above 37° C. (skin temperature as measured in the axilla area). The term "liquid" as used herein, unless otherwise specified, refers to those materials that are liquid at or below 37° C. As used herein, a material is determined to be a solid or a liquid at 37° C. by evaluating that material in a finished cosmetic stick composition using Differential Scanning Calorimetry (DSC). For example, A Perkin Elmer Model DSC-7, manufactured by Perkin Elmer Corporation, 761 Main Street, Norwalk Conn., can be used to measure a melting profile of the desired material. This is done by preparing a 20 mg sample in a volatile sample pan arrangement of the desired finished product to be tested. The heating curve is generated at 5° C./minute and is analyzed by measuring the partial area that melts below 37° C., and those showing at least 10% of the DSC curve below 37° C. are "liquids" and those showing less than 10% of the DSC curve below 37° C. are "solids."

The term "skin temperature" as used herein refers to the temperature of the axilla or other area of the skin, which is generally at or slightly below a typical body temperature of about 37° C.

The term "ambient conditions" as used herein refers to surrounding conditions under about one (1) atmosphere of pressure, at about 50% relative humidity, and at about 25° C., unless otherwise specified. All values, amounts and measurements described herein are obtained under ambient conditions unless otherwise specified.

The term "volatile" as used herein refers to those materials which have a measurable vapor pressure at 25° C. Such vapor pressures will typically range from about 0.01 mmHg to about 6 mmHg, more typically from about 0.02 mmHg to about 1.5 mmHg, and have an average boiling point at one (1) atmosphere of pressure (atm) of less than about 250° C., more typically less than about 235° C. at one (1) atm. Conversely, the term "non volatile" refers to those materials which are not "volatile" as defined herein.

The cosmetic stick compositions of the present invention can comprise, consist of, or consist essentially of the essential elements and limitations of the invention described herein, as well as any of additional or optional ingredients, components, or limitations known or otherwise effective for use in the such compositions.

All percentages, parts and ratios are by weight of the total composition, unless otherwise specified. All such weights as they pertain to listed ingredients are based on the specific ingredient level and, therefore, do not include solvents, carriers, by-products, filler or other minor ingredients that may be included in commercially available materials, unless otherwise specified.

Product Hardness

The cosmetic stick compositions of the present invention preferably have a product hardness of at least about 600 gram.force, most typically from about 600 gram.force to about 5,000 gram.force, preferably from about 750 gram.force to about 2,000 gram.force, more preferably from about 800 gram.force to about 1,400 gram.force.

The term "product hardness" or "hardness" as used herein is a reflection of how much force is required to move a penetration cone a specified distance and at a controlled rate into a cosmetic stick composition under the following test conditions. Higher values represent harder product, and lower values represent softer product. These values are measured at 27° C., 15% relative humidity, using a TA-XT2 Texture Analyzer, available from Texture Technology Corp., Scarsdale, N.Y., U.S.A. The product hardness value as used herein represents the peak force required to move a standard 45° angle penetration cone through the composition for a distance of 10 mm at a rate of 2 mm/second. The standard cone is available from Texture Technology Corp., as part number TA-15, and has a total cone length of about 24.7 mm, angled cone length of about 18.3 mm, a maximum diameter of the angled surface of the cone of about 15.5 mm. The cone is a smooth, stainless steel construction and weighs about 17.8 grams.

Cosmetic Actives

The cosmetic stick compositions of the present invention comprise from about 0.01% to about 60% by weight of a cosmetic active. Suitable actives include any known or otherwise effective cosmetic active that is compatible with the essential ingredients of the cosmetic sticks of the present invention, or which do not otherwise unduly impair the product performance thereof.

Cosmetic actives suitable for use in the compositions of the present invention include moisturizers, emollients, perfumes or fragrances, skin conditioners, antiperspirants, antioxidants, vitamins, anti-wrinkle products, surfactants, pharmaceuticals, deodorants, colorants, pigments, sunscreens or other photo protectants, and any other inert or active material intended or otherwise suitable for topical application to the skin.

Non-limiting examples of cosmetic actives suitable for use herein are described in U.S. Pat. No. 6,001,377 (SaNogueira, Jr. et al.), U.S. Pat. No. 6,024,942 (Tanner et al.), U.S. Pat. No. 6,013,271 (Doughty et al.), and U.S. Pat. No. 6,013,270 (Hargraves et al.), U.S. Pat. No. 6,013,248 (Luebbe et al.) U.S. Pat. No. 5,976,514 (Guskey et al.), which descriptions are hereby incorporated herein by reference.

Specific examples of cosmetic actives suitable for use herein include antiperspirant and deodorant actives as described herein, perfumes and frangrances, antimicrobials (antibacterial, antifungal), steroidal anti-inflammatory materials (e.g., hydrocortisone), non-steroidal anti-inflammatory materials, vitamins and derivatives thereof (e.g., thiamin, riboflavin, niacin, pyridoxine, vitamin A, vitamin D, vitamin E, vitamin K), hydroxy and alpha-hydroxy acids (e.g., salicylic acid, citric acid), moisturizers (e.g., silicone and non-silicone), and the like.

Non-limiting embodiments of the cosmetic stick compositions of the present invention include lipsticks, foundations and makeup, antiperspirant and deodorant sticks, suncreen or other photoprotective sticks, emollient sticks, health care actives delivered from a solid stick (e.g., steroidal and non-steroidal anti-inflammatory agents, analgesic stick, etc.), or any other solid stick embodiment from which a desired material, skin active or inert, is incorporated into for topical delivery to the skin.

Antiperspirant and Deodorant Active

The antiperspirant and deodorant embodiments of the present invention comprise an antiperspirant and/or deodorant active suitable for application to human skin. The active in the composition may be solubilized or in the form of solid particulates or dispersed liquid droplets. The concentration of active in the composition should be sufficient to provide the desired perspiration wetness and/or deodorant control.

The antiperspirant and deodorant embodiments of the present invention preferably comprise antiperspirant and/or deodorant active at concentrations ranging from about 0.1% to about 50%, more preferably from about 5% to about 35%, even more preferably from about 7% to about 30%, by weight of the composition. These weight percentages are calculated on an anhydrous metal salt basis exclusive of water and any complexing agents such as glycine, glycine salts, or other complexing agents.

The antiperspirant active for use in the compositions of the present invention include any compound, composition or other material having antiperspirant activity. Preferred antiperspirant actives include astringent metallic salts, especially the inorganic and organic salts of aluminum, zirconium and zinc, as well as mixtures thereof. Particularly preferred are the aluminum-containing and/or zirconium-containing materials or salts, such as aluminum halides, aluminum chlorohydrate, aluminum hydroxyhalides, zirconyl oxyhalides, zirconyl hydroxyhalides, and mixtures thereof.

Preferred aluminum salts for use in the antiperspirant and deodorant embodiments include those which conform to the formula:

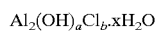

$$Al_2(OH)_aCl_b \cdot xH_2O$$

wherein a is from about 2 to about 5; the sum of a and b is about 6; x is from about 1 to about 6; and wherein a, b, and x may have non-integer values. Particularly preferred are the aluminum chlorohydroxides referred to as "5/6 basic chlorohydroxide", wherein a=5, and "2/3 basic chlorohydroxide", wherein a=4. Processes for preparing aluminum salts are disclosed in U.S. Pat. No. 3,887,692, Gilman, issued Jun. 3, 1975; U.S. Pat. No. 3,904,741, Jones et al., issued Sep. 9, 1975; U.S. Pat. No. 4,359,456, Gosling et al., issued Nov. 16, 1982; and British Patent Specification 2,048,229, Fitzgerald et al., published Dec. 10, 1980, all of which are incorporated herein by reference. Mixtures of aluminum salts are described in British Patent Specification 1,347,950, Shin et al., published Feb. 27, 1974, which description is also incorporated herein by reference.

Preferred zirconium salts for use in the antiperspirant and deodorant embodiments include those which conform to the formula:

$$ZrO(OH)_{2-a}Cl_a \cdot xH_2O$$

wherein a is from about 1.1 to about 2.0; x is from about 1 to about 8; and wherein a and x may both have non-integer values. These zirconium salts are described in Belgian Pat. No. 825,146, Schmitz, issued Aug. 4, 1975, which description is incorporated herein by reference. Particularly preferred zirconium salts are those complexes which additionally contain aluminum and glycine, commonly known as ZAG complexes. These ZAG complexes contain aluminum chlorohydroxide and zirconyl hydroxy chloride conforming to the above described formulas. Such ZAG complexes are described in U.S. Pat. No. 3,679,068, Luedders et al., issued Feb. 12, 1974; Great Britain Patent Application 2,144,992, Callaghan et al., published Mar. 20, 1985; and U.S. Pat. No. 4,120,948, Shelton, issued Oct. 17, 1978, all of which are incorporated herein by reference.

The antiperspirant and deodorant embodiments of the present invention can also be formulated with deodorant active in addition to or in place of the antiperspirant active described hereinbefore. The term "deodorant active" as used herein includes antimicrobial agents (e.g. bacteriocides, fungicides), malodor-absorbing materials, perfume chemicals that deodorize or mask body odor or which otherwise provide the desired fragrance, or combinations thereof. The concentration of deodorant active can vary with the particular active selected, but preferably ranges from about 0.1% to about 10%, more preferably from about 0.1% to about 5%, by weight of the composition.

Preferred deodorant actives are antimicrobial agents, non-limiting examples of which include cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, trimethyl ammonium chloride, sodium aluminum chlorohydroxy lactate, triethyl citrate, tricetylmethyl ammonium chloride, 2,4,4'-trichloro-2'-hydroxy diphenyl ether (triclosan), 3,4,4'-trichlorocarbanilide (triclocarban), diaminoalkyl amides such as L-lysine hexadecyl amide, heavy metal salts of citrate, salicylate, and piroctose, especially zinc salts, and acids thereof, heavy metal salts of pyrithione, especially zinc pyrithione, zinc phenolsulfate, farnesol, phenoxyethanol, and combinations thereof. Most preferred are triclosan and triclocarban.

Perfumes as deodorant actives suitable for use in the compositions of the present invention include any topical material that is known for or otherwise effective in masking malodor associated with perspiration, or which otherwise provides the composition or applied surface (e.g., skin) with the desired fragrance.

Solid Triglyceride Gellant

The cosmetic stick compositions of the present invention comprise a solid triglyceride gellant, wherein the solid triglyceride gellant is substantially free of long range crystalline order as formulated within the composition. Any triglyceride gellant that is known or otherwise effective for use in topical products is suitable for use herein, provided that it can also be formulated to have the requisite crystalline order within the composition. The concentration of the triglyceride gellant in the composition ranges from about 1% to about 60%, preferably from about 5% to about 30%, even more preferably from about 10% to about 26%, by weight of the composition.

The triglyceride gellant component of the composition of the present invention is characterized herein in terms of its crystalline order as formulated within the finished product rather than its crystalline form prior to and during formulation. It is expected that the triglyceride gellant materials prior to or during formulation would typically have a crystalline order or lack of crystalline order that is substantially different than the final crystalline order of the triglyceride in the finished product.

The solid triglyceride gellant for use in the composition must be a solid at or above human skin temperature (37° C.), either inherently (preferred) or as formulated within the finished composition. The solid triglyceride gellant must also be inherently polymorphic and be capable of being formulated into the composition as a solid matrix that is substantially free of long range crystalline order as defined herein. Solid triglyceride gellants that have the above-described characteristics will most typically be unsubstituted triglycerides or mixtures of unsubstituted triglycerides that correspond to the following formula:

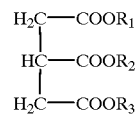

wherein R1, R2 and R3 are the same or different, and are unsubstituted hydrocarbon moieties that are preferably in the form of saturated alkyl groups. These triglycerides will most typically be in the form triglyceride mixtures wherein R1, R2 and R3 are alkyl groups having from 2 to 30 carbon atoms, and wherein the average number of carbon atoms per alkyl group per triglyceride molecule [(R1+R2+R3)/3] ranges from about 16 to about 24, more preferably from about 18 to about 22.

These solid, unsubstituted, triglyceride gellants are most typically obtained or derived from fully hydrogenated fats characterized as: (1) vegetable fats and oils such as soybean, corn, sunflower, high erucic acid rapeseed, low erucic acid rapeseed, canola, crambe, meadowfoam, cottonseed, olive, safflower, sunflower, sesame seed, nasturtium seed, tiger seed, ricebran, wallflower, and mustard seed; (2) meat fats such as tallow or lard; (3) marine oils such as menhaden, pilcherd, sardine, whale or herring; (4) nut fats and oils such as coconut, palm, palm kernel, babassu kernel, or peanut, Chinese Vegetable Tallow; (5) milkfat, butterfat; (6) cocoa butter and cocoa butter substitutes such as shea, or illipe butter; (7) structured triglycerides fats made from natural and synthetic routes; and (8) synthetic triglycerides made from hydrocarbon sources.

Specific nonlimiting examples of solid, unsubstituted triglyceride gellants suitable for use herein include tristearin, fully hydrogenated high erucic acid rapeseed oil (e.g., HEAR Oil, CanAmera, Canada), fully hydrogenated CRAMBE oil, and tribehenin (e.g., Syncrowax HR-C, Croda). Most preferred is fully hydrogenated high erucic acid rapeseed oil. It has been found that the solid cosmetic compositions of the present invention, when such compositions contain the preferred HEAR Oil as a suspending agent regardless of its polymorphic phase, have good product hardness and application cosmetics.

The cosmetic stick compositions may further comprise other gellant materials in addition to and other than the triglyceride gellants described herein, except that at least about 50%, preferably at least about 75%, by weight of the total gellant concentration in the composition must be the triglyceride gellants as described herein.

It is believed that at least most of the solid triglycerides described above do not inherently form the desired crystalline phase within the cosmetic stick compositions or do not otherwise form and remain within the desired crystalline phase over extended periods of time. The triglyceride gellants as formulated within the compositions of the present invention contain the requisite crystalline phase and maintain or are formulated to maintain that phase over prolonged periods of time, so that the product should remain substantially free of long range crystalline order over periods of time ranging from 1, 3, 6, and 12 months after formulation and packing.

The crystalline form of the triglyceride gellant, for purposes of defining the compositions of the present, are measured at least 3 months after formulation, preferably at between 3 and 6 months after formulation, most preferably at 6 months after formulation. Although many triglyceride sticks suggested in the literature may be substantially free of long range crystalline order immediately after formulation, these compositions will typically begin a phase shift immediately after formulation so that at 3 months or more after formulation they will no longer be substantially free of long range crystalline order. And because of this type of crystalline triglyceride phase shift to a long range crystalline order, these prior art formulations will become soft and lose much of their original product hardness over time.

In maintaining their intended crystalline form at or beyond 3 months from formulation, however, the compositions of the present invention also maintain or are formulated to maintain their product hardness value over time within the desired range, such that the product hardness for the compositions of the present invention preferably do not change by more than about 200 gram.force, more preferably by not more than about 100 gram.force, as measured at 0 and 6 months, more preferably as measured at 1 and 3 months, after formulation, or preferably over any 1, 2 or 3 month interval within the first 12 months after formulation.

Any known or otherwise effective method of formulating triglyceride solids to be substantially free of long range crystalline order over extended periods of time as described above can be applied to the formulation and manufacture of the cosmetic stick compositions of the present invention. Such methods are well known in the edible fat and shortening arts, although it is believed that their reapplication to cosmetic sticks has not heretofore been described. Examples of suitable methods are described in greater detail hereinafter.

X-ray Diffraction Methodology

The triglyceride crystalline phase within the cosmetic stick compositions of the present invention are determined in accordance with the following x-ray diffraction methodology. The various techniques used in the methodology are generally well known in the analytical arts, and are used herein to identify and quantify long range triglyceride crystalline order in the compositions of the present invention.

The following x-ray equipment is used in the diffraction methodology: (1) Philips PW1830 HT Generator w/PW1821 Multi-purpose Sample Stage, (2) Philips PW1397/60 Theta/2-Theta drive and Scintillation Counter, and (3) Philips PW1877 Automated Powder Diffraction Software Program v. 3.5B. Specific instrument parameters are set to divergence slit-¼°; scatter slit ¼°; mask 10 mm; receiving slit 0.05 mm; sample holder 15 mm×20 mm (Philips p/n PW1172); step size 0.05° 2-theta; start angle 1° 2-theta; end angle 3° 2-theta; time per step 10 sec; anode Cu; generator tension 45 kV; and generator current 40 mA.

A external reference standard for use in the methodology is prepared by heating a tribehenin sample (99% tribehenin; Sigma T-7904, Lot# 99H5180) in a 105° C. oven until completely melted. While still molten, the melted tribehenin is then placed in a dewer containing liquid nitrogen until completely solid. The solidified tribehenin is ground to a fine powder using a mortar and pestle. The fine tribehenin powder is placed into a 15 mm×20 mm sample holder (Philips p/n PW1172) and pressed into the holder using a glass microscope slide. All of the excess sample is removed using a knife edge. The holder containing the prepared sample, which is now the external reference standard, is then examined to make sure the surface of the sample is flush with the top of the holder prior to obtaining the x-ray diffraction pattern of the newly prepared external reference standard.

The composition of the present invention, or any other product for evaluation hereunder, is then prepared for x-ray diffraction analysis, and the results of which are then compared to the x-ray diffraction pattern for the external reference standard. The product or composition for analysis is first placed into a 15 mm×20 mm sample holder (Philips p/n PW1172) and then pressed into the holder using a glass microscope slide. The holder is then examined to assure that the sample is flush with the top of the holder prior to obtaining an x-ray diffraction pattern.

X-ray diffraction patterns are obtained for each product sample of interest, and then compared and evaluated relative to the x-ray diffraction pattern of the external reference standard described hereinbefore. The x-ray diffraction patterns are recorded and evaluated for each product sample in terms of peak area and height information by importing the x-ray diffraction patterns of both the external reference standard and the product sample of interest into a BioRad WinIR software package, v. 4.14 Level II, assigning a best fit baseline to the curve(s), integrating the area under the curve(s), and measuring the height of the curve(s), between 1 and 3 degrees 2-theta.

The triglyceride gellant described herein is substantially free of long range crystalline order, wherein such order or the absence of it is characterized by the x-ray diffraction analysis described herein. The product containing the triglyceride gellant is considered for purposes of defining the compositions of the present invention to be substantially free of long range crystalline order with respect to the triglyceride gellant material therein when any one or more of the following x-ray diffraction characteristics is noted.

In one embodiment of the cosmetic stick compositions of the present invention, the triglyceride gellant and/or product containing the triglyceride gellant is characterized as substantially free of long range crystalline order by an average AUC (area under the curve) at between 1° and 3° 2-theta that is less than about 6%, preferably less than about 5%, more preferably less than about 4%, of the corresponding average AUC for the external reference standard. In this context, the average AUC is determined for the sample product and for the external reference standard from a 10 sample average, each sample being prepared as described herein.

In yet another embodiment of the cosmetic stick compositions of the present invention, the triglyceride gellant and/or product containing the triglyceride gellant is characterized as substantially free of long range crystalline order by an average peak height at between 1° and 3° 2-theta of less than about 4%, preferably less than about 3%, even more preferably less than about 2%, of the corresponding average peak height of the external reference standard. In this context, the average peak height is determined for the product sample and for the external reference standard from a 10 sample average, each sample being prepared as described above.

The x-ray diffraction characteristics described herein, including average AUC and peak height values described above, must be determined or otherwise characterized from the triglyceride gellant and/or product containing the gellant at 3 months after formulation, preferably between about 3 and 12 months, more preferably at 6 months after formulation.

Liquid Carrier

The cosmetic stick compositions of the present invention comprises from about 10% to about 95%, preferably from about 20% to about 80%, more preferably from about 30% to about 70%, by weight of a liquid carrier suitable for topical application. The carrier may be aqueous or anhydrous, but is preferably anhydrous.

The liquid carrier preferably comprises a volatile silicone liquid. The concentration of the volatile silicone ranges from about 10% to about 90%, more preferably from about 15% to about 65%, even more preferably from about 30% to about 60%, by weight of the cosmetic stick composition. The volatile silicone may be a cyclic, linear or branched chain silicone having the requisite volatility as defined herein. Non-limiting examples of suitable volatile silicones are described in Todd et al., "Volatile Silicone Fluids for Cosmetics", Cosmetics and Toiletries, 91:27–32 (1976), which descriptions are incorporated herein by reference. Preferred among these volatile silicones are the cyclic silicones having from about 3 to about 7, more preferably from about 5 to about 6, silicon atoms. Most preferably are those which conform to the formula:

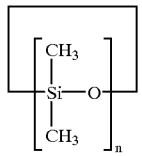

wherein n is from about 3 to about 7, preferably from about 5 to about 6, most preferably 5. These volatile cyclic silicones generally have a viscosity value of less than about 10 centistokes. All viscosity values described herein are measured or determined under ambient conditions, unless otherwise specified. Examples of suitable volatile silicones for use herein include Cyclomethicone D-5 (commercially available from G. E. Silicones); Dow Corning 344, and Dow Corning 345 (commercially available from Dow Corning Corp.); and GE 7207, GE 7158 and Silicone Fluids SF-1202 and SF-1173 (available from General Electric Co.).

Other suitable liquid carriers include non-volatile silicones. These non-volatile silicone carriers are preferably linear and include those which conform to either of the formulas:

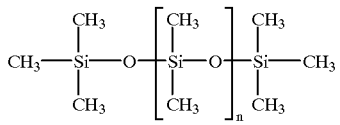

or

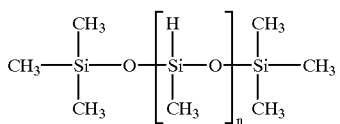

wherein n is sufficiently large to render the material non-volatile. These linear silicone materials will generally have viscosity values of from about 10 centistoke to about 100,000 centistoke, preferably from about 10 to about 500 centistoke, more preferably from about 10 centistoke to about 200 centistoke, even more preferably from about 10 centistoke to about 50 centistoke, as measured under ambient conditions. Examples of non-volatile, linear silicones suitable for use in the cosmetic stick compositions include Dow Corning 200, Dow Corning 225, Dow Corning 1732, Dow Corning 5732, Dow Corning 5750 (available from Dow Corning Corp.); and SF-96, SF-1066 and SF18(350) Silicone Fluids (available from G.E. Silicones).

Other suitable liquid carriers include volatile, nonpolar hydrocarbon liquids. In this context, the term "nonpolar" means that these volatile hydrocarbon liquids have a solubility parameter of less than about 7.5 $(cal/cm^3)^{0.5}$, most typically about 5.0 $(cal/cm^3)^{0.5}$ to less than about 7.5 $(cal/cm^3)^{0.5}$. These volatile, nonpolar hydrocarbon liquids preferably contain only hydrogen and carbon and therefore preferably contain no functional groups. Solubility parameters as described above are determined by methods well known in the chemical arts for establishing the relative polar character of a solvent or other material. A description of solubility parameters and means for determining them are described by C. D. Vaughan, "Solubility Effects in Product, Package, Penetration and Preservation" 103 Cosmetics and Toiletries 47–69, October 1988; and C. D. Vaughan, "Using Solubility Parameters in Cosmetics Formulation", 36 J. Soc. Cosmetic Chemists 319–333, September/October, 1988, which descriptions are incorporated herein by reference.

The nonpolar, volatile hydrocarbon liquid as a liquid carrier for use in the composition of the present invention is preferably a liquid paraffin and/or isoparaffin having the requisite volatility and nonpolar character. The nonpolar, volatile hydrocarbon liquids can have a cyclic, branched and/or chain configuration, and can be saturated or unsaturated, preferably saturated.

Preferred volatile, nonpolar hydrocarbon liquids are branched chain hydrocarbons at a concentration of from about 1% to about 40%, more preferably from about 1% to about 20%, by weight of the composition, and having from about 6 to about 40 carbon atoms, preferably from about 6 to about 20 carbon atoms. These preferred hydrocarbon liquids will most typically be formulated as a combination of two or more of the above-described branched chain hydrocarbons, wherein the combination of two or more hydrocarbons have different molecular weights, number of carbon atoms, and/or chain configurations. Specific nonlimiting examples of such combinations include the isoparaffins available from Exxon Chemical Company, Baytown, Tex. U.S.A, sold as Isopar M (C13–C14 Isoparaffin), Isopar C (C7–C8 Isoparaffin), Isopar E (C8–C9 Isoparaffin), Isopar G (C10–11 Isoparaffin), Isopar L (C11–C13 Isoparaffin), Isopar H (C11–C12 Isoparaffin), and combinations thereof. Other nonlimiting examples of suitable branched chain hydrocarbons include Permethyl 99A (C12, isododecane), Permethyl 101A (C16, isohexadecane), Permethyl 102A (C20, isoeicosane), and combinations thereof. The Permethyl series are available from Presperse, Inc., South Plainfield, N.J., U.S.A. Other nonlimiting examples of suitable branched chain hydrocarbons include petroleum distallates such as those available from Phillips Chemical as Soltrol 130, Soltrol 150, Soltrol 170, and those available from Shell as Shell Sol-70, -71, and -2033.

Still other suitable isoparaffins include C9–C11 Isoparaffin, C9–C13 Isoparaffin, C9–C14 Isoparaffin, C10–C13 Isoparaffin, C12–C14 Isoparaffin, C13–C16 Isoparaffin, C14–C18 Isoparaffin, and hydrogenated polyisobutene available from Amoco as the Panalane Series and from Fanning Corporation as the Fancor P series.

Nonlimiting examples of other volatile, nonpolar hydrocarbon liquids suitable for use in the cosmetic stick compositions include paraffins such as dodecane, octane, decane and combinations thereof, and the Norpar series of paraffins available from Exxon Chemical Company such as Norpar-12, -13, and -15 and the Neosolve series of paraffins available from Shell. Yet another example includes C11–C15 alkanes/cycloalkanes, such as those available from Exxon as Exxsol D80.

Other suitable liquid carriers for use in the cosmetic stick compositions of the present invention include any liquid material suitable for use on human skin which is also compatible within the cosmetic stick formulation selected. Examples of some of the many suitable liquid carriers are described in Cosmetics, Science, and Technology, Vol. 1, 27–104, edited by Balsam and Sagarin (1972); U.S. Pat. No. 4,202,879 issued to Shelton on May 13, 1980; and U.S. Pat. No. 4,816,261 issued to Luebbe et al. on Mar. 28, 1989, which descriptions are incorporated herein by reference.

Optional Ingredients

The cosmetic stick compositions of the present invention may further comprise any optional material that is known for use in cosmetic compositions or other personal care products, or which are otherwise suitable for topical application to human skin.

Nonlimiting examples of such other optional materials include dyes or colorants, emulsifiers, distributing agents, residue masking agents, inert fillers, preservatives, surfactants, processing aides such as viscosity modifiers, wash-off aids, and so forth. Other suitable optional materials include other solid gellants or waxes in addition to and other than the solid triglyceride gellants described herein. Examples of such optional materials are described in U.S. Pat. No. 4,049,792 (Elsnau); U.S. Pat. No. 5,019,375 (Tanner et al.); and U.S. Pat. No. 5,965,113 (Guskey), which descriptions are incorporated herein by reference.

Methods of Manufacture

The cosmetic stick compositions of the present invention may be prepared by any known or otherwise effective technique, suitable for providing a cosmetic stick composition having the product characteristics described herein, provided that the method also includes control over the crystalline phase of the triglyceride gellant so that the triglyceride gellant as formulated into the composition is substantially free of long range crystalline order as described herein.

A preferred method for controlling the crystalline phase of the triglyceride gellant of the compositions herein is by the addition and use of materials that are well known for or otherwise effective in retarding phase transitions in triglycerides. Examples of such materials and use are generally described in "Crystallization And Polymorphism Of Fats and Fatty Acids" edited by Nissim Garti and Kiyotaka Sato, volume 31 (1988), which description is hereby incorporated by reference. Specific non-limiting examples of such materials include surfactants, emulsifiers, C14–26 fatty acids, C12–30 monoglycerides and/or C12–30 diglycerides, fully and partially esterified polyglycerol esters and derivatives thereof, sorbitan esters and derivatives thereof (e.g., sorbitan tristearate, sorbitain monostearate, sorbitan monopalmitate), dibenhenate and/or distearine, behenic acid, stearic acid, lecithin and fractions of lecithin, structured forms of mono and diglycerides, mixtures of saturated triglycerides and their breakdown components made through enzymatic digestion or other cleavage/cracking processes, structured mono, diglyceride and triglyceride mixtures synthesized from hydrocarbons, and combinations thereof.

Especially preferred for controlling triglyceride crystallization in the compositions herein include the use of fully hydrogenated HEAR oil (high erucic acid rapeseed oil) with Syncrowax HGLC (C18–36 Acid Triglyceride) at a weight ratio of from about 4:1 to about 1:1. Other preferred materials include fully hydrogenated HEAR oil in combination with dibehenin (Compritol 888, manufactured by Gattefosse) at a weight ratio of from about 4:1 to about 1:1, and fully hydrogenated HEAR oil in combination with HEAR oil mono and diglycerides at a weight ratio of from about 4:1 to about 1:1. Most preferred is the combination of fully hydrogenated HEAR oil and Syncrowax HGLC at a weight ratio of about 4:1, wherein the composition contains 15% by weight of the fully hydrogenated HEAR and 3.75% by weight of the Syncrowax HGLC.

Another method of controlling the crystalline phase of the triglyceride gellant is by controlling the rate of cooling of the liquefied triglyceride solid during formulation so that the peak melting point as measured by DSC (Differential Scanning Calorimetry) for the resulting triglyceride phase in the formulation is between about 57° C. and about 60° C. and the resulting triglyceride gellant in the formulation is substantially free of long range crystalline order as determined by the x-ray phase methodology described herein. Methods for determining DSC values for solid materials are well known in the chemical arts, and can be easily reapplied to the cosmetic stick compositions of the present invention. For example, a Perkin Elmer Model DSC-7, manufactured by Perkin Elmer Corporation, 761 Main Street, Norwalk Conn., can be used to measure a melting profile of the desired material This is done by preparing a 20 mg sample in a volatile sample pan arrangement of the desired finished product to be tested. The heating curve (DSC curve) is generated at 5° C. per minute.

The antiperspirant and deodorant stick embodiments of the present invention can be formulated, for example, by mixing the carrier liquid(s) under ambient conditions, or under conditions sufficient to render the admixture fluid or liquid, and adding the triglyceride and other non-active solids to the mixture and then heating the resulting mixture sufficiently to liquefy the added materials and to form a single phase liquid, e.g. 85° C. Antiperspirant or other similar solid cosmetic active, if any, are then added to and dispersed throughout the heated, single phase liquid before allowing the resulting combination to cool to approximately 78° C., at which point perfumes or other similar materials are mixed into the combination, which is then allowed to cool to 60° C. which is just above the solidification temperature of the formulation matrix at a cooling rate of from about 0.5° C. per minute to about 200° C. per minute (rate can be selected to obtain a solidified triglyceride matrix that is substantially free of long range crystalline order) before being poured into dispensing packages and allowed to solidify under ambient or other selected condition to obtain the desired crystalline form of the triglyceride gellant.

The present invention, therefore, is also directed to methods of making the cosmetic compositions of the present invention, wherein the compositions are made by any method which controls solid triglyceride crystallization to the desired end results described herein. The cosmetic stick embodiments of the present invention may then be applied topically to the desired area of the skin in an amount effective to provide the desired result.

EXAMPLES

The following non-limiting examples illustrate specific embodiments of the cosmetic stick compositions of the present invention, including methods of manufacture and use. Each of the exemplified compositions are prepared in a similar manner by combining the solid gellants and liquid carriers in a vessel equipped with a heat source. The combined solids and liquids are heated to a temperature ranging from 85° C. to 96° C. and agitated to dissolve the solid gellants until the mixture forms a homogeneous clear to slightly cloudy solution, at which point the antiperspirant or other cosmetic active is typically added to and dispersed throughout the heated solution while maintaining mixing. The resulting heated combination is then circulated through a scraped wall heat exchanger and cooled to 62° C. before filling the cooled mixture into plastic dispensing canisters and allowed to cool and solidify within the canisters over a 20 minute period (cooling rate of 2° C./min) through a forced air cooling tunnel having an air temperature of 21 ° C.

Each of the exemplified compositions contain a solid triglyceride crystalline matrix that is substantially free of and remains substantially free of long range crystalline order over prolonged periods, e.g., at 1, 3, 6, 12 and 24 months, or any 1, 2 or 3 month interval therein, and maintains 90–100% of their initial product hardness values (e.g., as measured at 24 hours after manufacture) over the same prolonged intervals. Each of the exemplified compositions is applied topically to the desired area of the skin, in accordance with the methods of use described herein.

All exemplified amounts are weight percentages based upon the total weight of the cosmetic stick composition, unless otherwise specified.

TABLE 1

Antiperspirant and Deodorant Sticks

| Ingredient | Example 1 | Example 2 | Example 3 | Example 4 |
|---|---|---|---|---|
| Al Zr Trichlorhydrex Glycinate | 20.00 | 20.00 | 25.25 | 24.00 |
| Cyclopentasiloxane | 45.50 | 45.50 | 40.25 | 41.50 |
| Tribehenin (Syncrowax HR-C)[1] | 0.00 | 15.00 | 15.00 | 15.00 |
| C18–36 Acid Triglyceride (Syncrowax HGLC)[2] | 3.75 | 3.75 | 3.75 | 3.75 |
| Perfume | 0.75 | 0.75 | 0.75 | 0.75 |
| C13–14 Isoparaffin (Isopar M)[3] | 10.00 | 10.00 | 10.00 | 10.00 |
| Dimethicone 50 cs | 5.00 | 5.00 | 5.00 | 5.00 |
| Fully Hydrogenated High Erucic Acid Rapeseed Oil[4] | 15.00 | 0.00 | 0.00 | 0.00 |
| Totals | 100.00 | 100.00 | 100.00 | 100.00 |
| Product hardness (gram · force) | 870 | 870 | 1025 | 1050 |

[1]Croda, Inc., New York, New York, USA
[2]Croda, Inc., New York, New York, USA
[3]Exxon Chemical Company, Baytown, Texas, USA,
[4]CanAmera, Canada

TABLE 2

Antiperspirant and Deodorant Sticks

| Ingredient | Example 5 | Example 6 | Example 7 |
|---|---|---|---|
| Al Zr Trichlorhydrex Glycinate | 25.00 | 25.00 | 20.00 |
| Cyclopentasiloxane | 50.50 | 40.50 | 48.00 |
| Tribehenin (Syncrowax HR-C)[1] | 0.00 | 0.00 | 10.00 |
| C18–36 Acid Triglyceride (Syncrowax HGLC)[2] | 3.75 | 0.00 | 2.50 |
| Perfume | 0.75 | 0.75 | 0.75 |
| C13–14 Isoparaffin (Isopar M)[3] | 0.00 | 10.00 | 10.00 |
| Dimethicone 50 cs | 5.00 | 5.00 | 5.00 |
| Fully Hydrogenated HEAR Oil[4] | 15.00 | 15.00 | 0.00 |
| C18–36 Acid Glycol Ester (Syncrowax ERL-C)[5] | 0.00 | 3.75 | 0.00 |
| Strahl And Pitsch Paraffin SP173[6] | 0.00 | 0.00 | 3.75 |
| Totals | 100.00 | 100.00 | 100.00 |
| Product hardness (gram · force) | 1050 | 1040 | 956 |

[1]Croda, Inc., New York, New York, USA
[2]Croda, Inc., New York, New York, USA
[3]Exxon Chemical Company, Baytown, Texas, USA,
[4]CanAmera, Canada
[5]Croda, Inc., New York, New York, USA
[6]Strahl & Pitsch, Inc., West Babylon, New York

TABLE 3

Analgesic Stick

| Ingredient | Weight % |
|---|---|
| Methyl Salicylate | 20% |
| Menthol | 10.00% |
| PAO 3004 | 45.00% |
| Fully Hydrogenated HEAR oil | 20.00% |
| Syncrowax HGLC | 5.00% |

TABLE 4

Moisturizing Emollient Stick

| Ingredient | Weight % |
|---|---|
| Tocopherol Acetate | 1.00% |
| Petrolatum | 20.00% |

TABLE 4-continued

Moisturizing Emollient Stick

| Ingredient | Weight % |
| --- | --- |
| PAO 3004 | 58.95% |
| Fully Hydrogenated HEAR oil | 15.00% |
| Syncrowax HGLC | 5.00% |
| Propyl Paraben | 0.05% |

TABLE 5

Sunscreen Stick

| Ingredient | Weight % |
| --- | --- |
| Cyclomethicone | 20.00% |
| Octylmethoxycinnamate | 7.50% |
| PAO 3004 | 34.50% |
| Fully Hydrogenated HEAR oil | 25.00% |
| Syncrowax HGLC | 5.00% |
| Benzophenone-3 | 3.00% |
| Octyl Salicylate | 5.00% |

TABLE 6

Cosmetic Stick

| Ingredient | Weight % |
| --- | --- |
| Cyclomethicone | 45.00% |
| Dimethicone | 20.00% |
| Zinc Oxide | 5.00% |
| Fully Hydrogenated HEAR oil | 25.00% |
| Syncrowax HGLC | 5.00% |

What is claimed is:

1. Cosmetic stick compositions comprising:
   (a) from about 0.01% to about 60% by weight of a cosmetic active;
   (b) from about 10% to about 95% by weight of a liquid carrier;
   (c) from about 1% to about 60% by weight of a solid, polymorphic, unsubstituted, triglyceride gellant,
   wherein the triglyceride gellant within the compositions is substantially free of long range crystalline order, and wherein the compositions have a product hardness of at least about 600 gram·force.

2. The composition of claim 1 wherein the composition is anhydrous and contains less than about 3% by weight of free or added water.

3. The composition of claim 1 wherein the composition is substantially free of long range crystalline order at about 6 months after formulation.

4. The composition of claim 3 wherein the composition at 6 months after formulation provides an x-ray diffraction pattern according to the X-ray Diffraction Methodology, wherein the pattern is characterized by an average area under the curve at between 1° and 3° 2-theta of less than about 4% of the corresponding average area under the curve for a 99% tribehenin external reference standard.

5. The composition of claim 3 wherein the composition at 6 months after formulation provides an x-ray diffraction pattern according to the X-ray Diffraction Methodology, wherein the pattern is characterized by an average peak height at between 1° and 3° 2-theta of less than about 2% of the corresponding average peak height of a 99% tribehenin external reference standard.

6. The compositions of claim 1 wherein the solid, polymorphic, unsubstituted triglyceride gellant comprises a solid triglyercide corresponding to the formula:

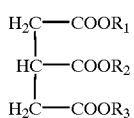

wherein R1, R2 and R3 are independently selected from saturated alkyl groups having from about 2 to about 30 carbon atoms, and wherein the average number of carbon atoms per saturated alkyl group as represented by the expression (R1+R2+R3)/3 is from about 16 to about 24.

7. The composition of claim 1 wherein the composition comprises from about 5% to about 30% by weight of the solid polymorphic triglyceride gellant.

8. The composition of claim 1 wherein the cosmetic active is selected from the group consisting of antiperspirants, antimicrobials, perfumes, moisturizers, emollients, antiperspirants, anti-oxidants, vitamins, surfactants, pharmaceuticals, deodorants, sunscreens, and combinations thereof.

9. The composition of claim 8 wherein the cosmetic active is an antiperspirant active selected from the group consisting of aluminum-containing active, zirconium-containing active, and combinations thereof.

10. The composition of claim 9 wherein the antiperspirant active within the composition is in the form of solid particulates.

11. The composition of claim 1 wherein the triglyceride gellant is selected from tristearin, fully hydrogenated high erucic acid rapeseed oil, hydrogenated low erucic acid rapeseed oil, tribehenin, and combinations thereof.

12. The composition of claim 11 wherein the triglyceride gellant is fully hydrogenated high erucic acid rapeseed oil.

13. The composition of claim 1 wherein the product hardness at 1 and 3 months after formulation differs by no more than 200 gram.force.

14. The composition of claim 1 wherein the product hardness does not change over any selected 30 day period following formulation by more than 100 gram.force.

15. The composition of claim 2 wherein the liquid carrier comprises a volatile cyclomethicone.

16. The composition of claim 15 wherein the liquid carrier comprises a nonvolatile silicone liquid.

17. The composition of claim 15 wherein the liquid carrier a volatile, non-polar, branched-chain hydrocarbon liquid at a concentration of from about 1% to about 40% by weight of the composition.

18. A method of controlling product hardness in a cosmetic stick composition containing solid, polymorphic, unsubstituted triglyceride gellants and having a product hardness of at least about 600 gram·force, wherein the method comprises formulating the cosmetic composition with a triglyceride gellant so that the gellant within the composition is substantially free of long range crystalline order at 3 months after formulation.

* * * * *